United States Patent

Willmen

[11] Patent Number: 5,868,744
[45] Date of Patent: Feb. 9, 1999

[54] ELECTROSURGICAL INSTRUMENT FOR THERAPEUTIC TREATMENT OF VARICES

[76] Inventor: Hans-Rainer Willmen, Nachtigallenstr. 22, D-41515 Grevenbroich, Germany

[21] Appl. No.: 737,103
[22] PCT Filed: Apr. 28, 1995
[86] PCT No.: PCT/EP95/01614
 § 371 Date: Oct. 25, 1996
 § 102(e) Date: Oct. 25, 1996
[87] PCT Pub. No.: WO95/29644
 PCT Pub. Date: Nov. 9, 1995

[30] Foreign Application Priority Data

Apr. 28, 1994 [DE] Germany ............. 44 14 807.0

[51] Int. Cl.$^6$ ..................... A61B 17/39
[52] U.S. Cl. ............. 606/50; 607/99; 607/116
[58] Field of Search ............. 606/42, 48, 50; 607/99, 116, 150; 600/373, 393

[56] References Cited

U.S. PATENT DOCUMENTS

| 1,814,791 | 7/1931 | Ende . | |
| 1,916,722 | 7/1933 | Ende . | |
| 1,943,543 | 1/1934 | McFadden . | |
| 2,611,365 | 9/1952 | Rubens . | |
| 3,301,258 | 1/1967 | Werner . | |
| 3,651,812 | 3/1972 | Samuels . | |
| 4,074,718 | 2/1978 | Morrison, Jr. | 606/48 |
| 5,403,311 | 4/1995 | Abele et al. | 606/50 |

*Primary Examiner*—Lee Cohen
*Attorney, Agent, or Firm*—Collard & 'Roe, P.C.

[57] ABSTRACT

An electrosurgical instrument is useful for therapeutic treatment of varices, especially small varicose dilatations of the cutaneous veins. A surgical instrument is provided for rapid, reliable and minimally discomforting therapy of small varicose dilatations of the cutaneous veins and similar disorders, ensuring the lowest possible rate of recidivism while minimizing side effects. The instrument has two fork-shaped protruding needle electrodes which connect to different poles of an electrical power source and which are each partially enclosed in an electrical insulating layer. The forward tip region of the needle electrodes is left open.

5 Claims, 2 Drawing Sheets

# ELECTROSURGICAL INSTRUMENT FOR THERAPEUTIC TREATMENT OF VARICES

BACKGROUND OF THE INVENTION

1. Field of the Invention

The invention relates to an electrosurgical instrument for the therapy of varices, in particular of small varicose dilatations of the cutaneous veins.

2. The Prior Art

Varices are understood to be veins extending along the surface of the body, which, in most cases, are pathologically dilatated lig bags or in the form of knots. Due to occupations requiring standing, overweight, tight garments or pregnancy, small varicose dilatations of the cutaneous veins of the legs develop particularly frequently from an innate weakness of the connective tissue. In view of the civilizationally conditioned increase in said promoting factors, more and more people suffer from the consequences of the primary varicosis caused thereby. In the advanced stage, varices are sometimes very painful and not infrequently lead to work disability. Therefore, the earliest possible therapeutic treatment of small varicose dilatations of the cutaneous veins and small varices is indicated.

According to the state of the art, the so-called sclerosing is commonly applied for the treatment of small varicose dilatations of the cutaneous veins. In this connection, following a prior injection of air, an obliterating agent is injected in the affected section of the veins. This is followed by a compression treatment, for example in the form of compression bandages or compression hoses.

The aforementioned method has the advantage that especially in the treatment of small varicose dilatations of the cutaneous veins, no surgical intervention is required. Otherwise, however, known obliterating methods lead to unsatisfactory results: Medicinal sclerosing often leads to more or less extensive spotted discolorations of the skin, which is not only perceived as annoying cosmetically, but also represents a psychic stress for the patient. Furthermore, the therapy is relatively protracted because several successive treatments are required at intervals of several days. Moreover, with sclerosing, the rate of recidivism is relatively high.

Furthermore, attempts have been made to therapeutically treat small varicose dilatations of the cutaneous veins by irradiation with laser light. These methods, however, have been insufficient heretofore, and permitted only minor cosmetic corrections. The laser therapy, according to the current state of knowledge, seems to hold only little promise for success for a comprehensive treatment of small varicose dilatations of the cutaneous veins and varices.

A method of treating varices is known from U.S. Pat. No. 3,301,258, which is based on the destruction of, the diseased section of the vein by means of electrical current (diathermy current). The instrument for carrying out the method, which is disclosed in the US-document as well, has two electrodes, which are electrically insulated against each other and arranged at the distal end of a small cylindrical probe, as well as means for generating and transmitting electrical current to said electrodes.

For treating the varix, the probe is inserted in the skin of the patient through a cut and subcutaneously guided on until the electrodes, for which provision is made at the distal end of the probe, have reached the site to be treated. Subsequently, an electrical current is permitted to flow through the electrodes; the heat generated in this connection leads to the destruction of the neighboring vein section. However, the surgical instrument for the treatment of varices according to the aforementioned US-patent is not suitable for ambulatory therapy because the surgical intervention connected therewith requires a hospital stay and leads to considerable stress for the patient.

A surgical instrument for us in diathermyand similar medical and surgical treatment is known from U.S. Pat. No. 1,943,543, said instrument consisting of a grip, an insulating sleeve, and two electrodes mounted on the grip. The two electrodes are surrounded by the insulating sleeve, and can be left free by displacing the sleeve. When the electrodes are inserted in the tissue to be treated, the insulating sleeve remains on the surface of the tissue, so that the electrode section projecting into the tissue remains uninsulated. The above surgical instrument is not suitable for the treatment of varices because due to the lack of insulation of the electrodes, current can flow along the surface of the skin, which leads to the formation of cosmetically disfiguring current marks.

From this results the problem of the invention, which is to provide the treating therapist with a surgical instrument permitting a therapy of varices with small varicose dilatations of cutaneous veins and the like, which can be carried out quickly and safely with as little stress as possible for the patient and with minimized side effects. In addition, the objective is to keep the rate of recidivism as low as possible.

For solving said problem, the invention proposes on the basis of the surgical instrument for the treatment of varices according to U.S. Pat. No. 3,301,258 that the instrument has two fork-like arranged, protruding needle electrodes, which are connectable to different poles of an electrical current source, and which each are partly enclosed by a thin electrical insulation layer, which leaves the forward tip zone of the needle electrodes free, whereby the transition from the tip zone to the insulated zone is substantially stepless.

SUMMARY OF THE INVENTION

In connection with the invention, the two needle electrodes are arranged next to each other in a way such that they form a two-pronged fork. In this connection, the two needle electrodes are fitted with a thin electrical insulating layer ending shortly before the metallic blank tip. The thinness of the insulating layer is selected in such a way that nearly no protruding step is formed at the transition to the uninsulated tip. Alternatively, the needle electrode can be shaped in its rear region in such a way that the insulation is sunk, which provides the insulated shaft and the tip of the needle electrode with the same cross section, i.e., the insulated part adjoins the uninsulated tip with nearly no transition. The two needle electrodes are electrically insulated against each other and connectable to an electrical current source via a connection cable. As a rule, an HF (high-frequency) power supply part is used, as it is known in electrosurgery, for example for heating tissue.

The special advantage of the invention results from the forklike arrangement of the needle electrode in combination with their part insulation. The bipolar coagulation fork formed according to the invention is simply inserted by the operator through the surface of the skin of the patient into the small varicose dilatation of the cutaneous vein, whereby the uninsulated tips of the two needle electrodes are arranged one after the other in the cross section of the pathologically dilatated vein. By applying an HF-voltage to the two needle electrodes, a high-frequency electrical current flows between the uninsulated needle tips along the small varicose dilatation of the cutaneous vein, into which the coagulation fork is inserted. What is accomplished in this way is that an electro-coagulation is carried out between the needle electrodes with narrow local limitation only within the region of the small varicose dilatation of the cutaneous vein.

Depending on the spacing of the needle electrodes from one another, it is thus possible to carried out a localized coagulation of small varicose dilatations of cutaneous veins is a precisely targeted and accurately pointed way. In this connection, the electro-coagulation represents an efficient method for completely obliterating small varicose dilatations of cutaneous veins even with a short duration of treatment, so that a low rate of recidivism, i.e., renewed formation of varices, is achieved.

The treatment can be carried out by the therapist in a simple and safe way. The patient himself/herself is stressed in this connection only to a small extent because the needle electrodes can be designed sufficiently thin, and the depth of penetration is low, as a rule. The transitionless connection of the metallic blank needle tips with the insulated shaft assures that the insertion of the coagulation fork is completely without any problems.

With the targeted and localized coagulation, it is advantageous, furthermore, that adjacent body tissue and fasciculi of nerves are practically not damaged by heating. Owing to the fact that the needle electrodes are fitted in their extension with an insulation, the electrical HF-current flow localized subcutaneously. In this connection, no current flows along the surface of the skin, so that no cosmetically disfiguring current marks appear.

The electrodes and the insulation are preferably manufactured from materials that assure compliance with the safety and protection regulations for the application of electrical current. It is particularly useful that such materials are thermally stable, so that they can be sterilized thermally.

According to an advantageous further development of the invention, provision is made that the needle electrodes are axially supported at the rearward end in insulating sleeves having a clearly larger cross section than the needle electrodes. Owing to such a design, the use of a coagulation fork according to the invention is further simpled and made safe in an advantageous way, because with such a design, a step is formed at the point of transition from the needle electrodes to the insulating sleeves, which step, when the coagulation fork is inserted, serves as a stop. If, for example, the needle electrodes project forwardly from the insulating sleeves by just a few millimeters, it is impossible to insert the needle electrodes by mistake too deep into the skin of the patient. If the length of the needle electrodes itself is adapted to the typical depth of small varicose dilatations of cutaneous veins, at which such varices extend under the surface of the skin, the therapy is particularly simple because the coagulation fork has to be inserted only up to the insulating sleeves.

Furthermore, according to a particularly advantageous embodiment, provision is made that the insulating sleeves form the legs of an approximately trouser-shaped electrode head, on which the needle electrodes are mounted on the leg-side directed forwardly, and which is connected rearwardly with a pencil-shaped grip piece. The advantage of the approximately trouser-shaped design of the electrode head is that the therapist has at any time an unobstructed view of the field of application. The handle, which is mounted rearwardly on the electrode head, and which is designed in the form of a pencil, assures that the instrument can be handled in a particularly good way, because it can then be guided and applied comfortably with one hand like an eating fork or a writing pen.

According to a preferred further development of the invention, provision is made that the electrode head and the grip piece have corresponding electrical and mechanical connection elements, which are detachably connectable with each other. In this embodiment, the grip piece has, for example an electrical plug connector, which is connected to the electrical feed cable, and into which the electrode head is pluggable. It is accomplished in this way that the electrode head can be exchanged quickly and without problems. This is especially important if, for example, electrode heads with needle electrodes having different lengths have to be used, and/or with needle electrodes with different spacings from each other. Furthermore, by exchanging the needle head, the instrument is immediately ready again for use, so that patients can be therapeutically treated one after the other without waiting periods. The exchanged electrode heads can then be sterilized again in the meantime.

For avoiding electrical losses, it is particularly useful that the electrical and mechanical connection elements are coaxial plug connectors. This, on the one hand, permits a low-loss passage of high-frequency ac current into the electrodes; on the other hand, such a plug connection is particularly safe to operate due to the symmetrical design, and it is safely fixed mechanically when elastic contacts are used.

In an advantageous embodiment, an electrical hand switch is arranged in the grip piece, such switch being integrated in the supply cables of the needle electrodes. A switch integrated in the grip piece has, for example a pressure or sliding contact. It is possible in this way to exactly control with the coagulation fork inserted the time and duration of the current flow by means of the hand guiding the instrument.

Alternatively, it is possible also to arrange in the supply cable of the needle electrodes a footswitch, which permits switching the instrument on and off without using the hands. This clearly simplifies the treatment because the coagulation fork according to the invention can be exactly guided with one hand, whereas, for example the skin tissue is lifted with the other hand.

BRIEF DESCRIPTION OF THE DRAWINGS

An exemplified embodiment of the invention is explained in greater detail in the following by reference to the drawings, in which.

DETAILED DESCRIPTION OF PREFERRED EMBODIMENT

Figure 1:
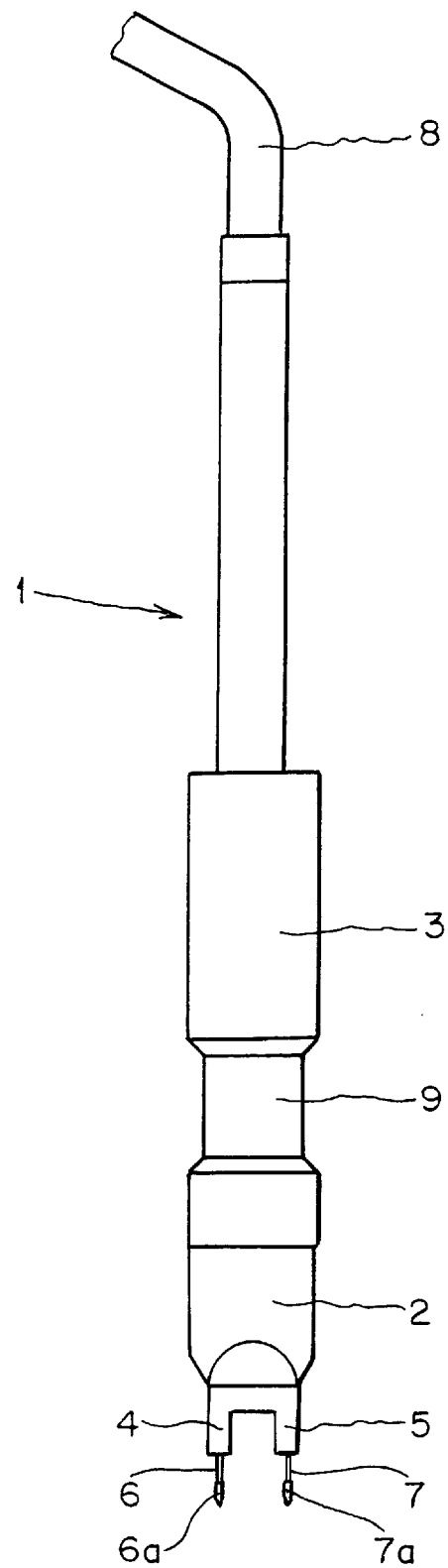
FIG. 1 shows an overall view of an instrument according to the invention.

In FIG. 1, the electrosurgical instrument, i.e., the bipolar coagulation fork as a whole is denoted by reference numeral 1. It substantially consists of an electrode head 2, which is inserted in a long-stretched, cylindrical pen-shaped grip piece 3.

In its forward zone, the electrode head 2 is designed approximately trouser-shaped. It substantially consists of insulating material. The legs of the electrode head 2 point parallel in the forward direction and are designed as the insulating sleeves 4 and 5. The needle electrodes 6 and 7 are mounted in the insulating sleeves 4 and 5 at the forward, blunt ends of the latter, protruding in the longitudinal direction. The needle electrodes 6 and 7 are consequently arranged approximately fork-like on the electrode head 2.

In their rearward zone, the needle electrodes 6 and 7 are coated with a thin electrical insulation layer, which is shown in the drawing by the black filling. The tips of the needle elctrodes 6 and 7, said tips being denoted by 6a and 7a, are metallic blank, i.e., uninsulated.

An electrical cable 8 feeds from the back into the grip piece 3, said cable being connected to an HF supply part not shown. In the interior of the grip piece 3, the lines of the cable 8 extend via a manual switch 9, which is designed as a ring switch contact, and into the electrode head 2, and end in the needle electrodes 6 and 7.

The electrode head 2 and the grip piece 3 are mechanically and electrically detachably connected with each other by way of connection elements not visible in this representation.

Figure 2:
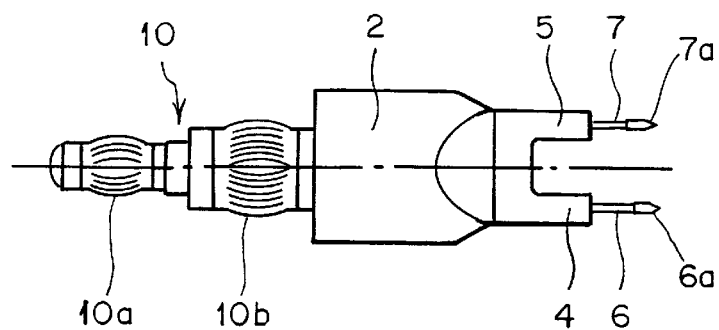
FIG. 2 shows the electrode head of the instrument according to FIG. 1.

In FIG. 2, the electrode head 2 according to FIG. 1 is shown removed from the grip piece 3. The coaxial plug connector 10 is clearly visible, said connector having the radially elastic ring contacts 10a and 10b. Said ring contacts are electrically conductively connected to the needle electrodes 6 and 7. The grip piece 3 according to FIG. 3 is fitted with a plug socket not shown in the drawing, said socket receiving the plug connector 10 and establishing the electrical connection and the mechanical locking.

Figure 3:
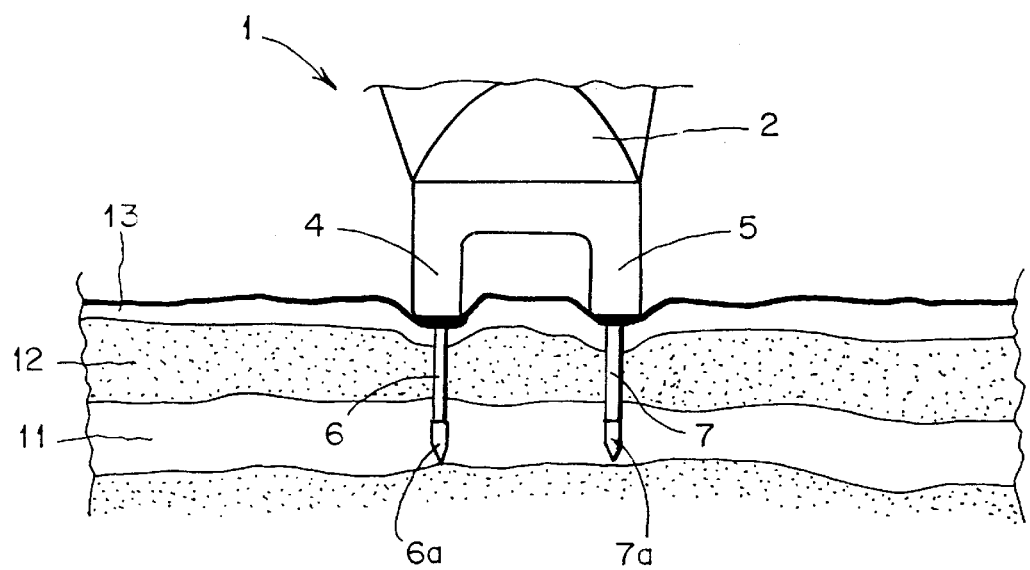
FIG. 3 shows a schematic sectional representation of varicose dilatations of a cutaneous vein, with an inserted electrode head according to FIG. 1 or FIG. 2.

FIG. 3 shows a schematic sectional representation of a typical treatment situation, in which the small varicose dilatations of the cutaneous vein 11 extend below the leather skin 12 and the top skin 13 of a human body.

The coagulation fork 1 with the needle electrodes 6 and 7 is inserted through the top skin 13 and the leather skin 12, namely in such a way that the tips 6a and 7a are present in the cross section of the varix 11 with small varicose dilatations of the cutaneous vein, with the insulating sleeves 4 and 5 resting with their blunt forward ends on the top skin 13 as a stop means.

The therapy by means of the bipolar coaguation fork 1 according to the invention can be carried out in a particularly simple and safe way: For such therapy, a suitable electrode head 2 is selected first, such head having needle electrodes 6 and 7 which, with respect to length and spacing from each other, are optimally adapted to the given purpose of application. The bipolar coaguation fork 1 is connected to a suitable HF supply unit via the electrical cable 8 and is thus ready for use.

Thereafter, the needle electrodes 6 and 7 are inserted in a varix 11 with small varicose dilatations of the cutaneous vein, which varix can be clearly seen to extend under the surface of the skin through the top skin 13 and the leather skin 12, namely to a depth until the insulating sleeves 4 and 5 of the electrode head 2 come to rest on the top skin 13. This is the situation shown in FIG. 3.

The needle electrodes 6 and 7 can not be inserted excessively deep because the insulating sleeves 4 and 5 form a stop. Due to the trouser-like design of the electrode head 2, the operator has a clear view of the varix with small varicose dilatations of the cutaneous vein extending between the needle electrodes 6 and 7.

By depressing the manual switch 9, an HF-voltage is applied to the needle electrodes 6 and 7. This causes an HF-current to flow via the electrolytically conductive body tissue along a direct line of connection between the blank tips 6a and 7a of the needle electrodes 6 and 7. Said imaginary line of connection extends within the varix 11 with small varicose dilatation of the cutaneous vein, so that consequently only the region of the varix 11 forms a current flow duct that is heated. Due to the narrowly limited, local heating, said varix is coagulated or dried out, i.e., obliterated within the region between the electrodes 6 and 7.

Due to the increase in the total electrical impedance occurring between the needle electrodes 6 and 7 as the varix 11 is being obliterated, the HF-current drops if the therapy was successful. This can be controlled by the therapist, for example with a current-measuring device, and the flow of current can be interrupted in due time by means of the switch 9.

The bipolar coagulation fork 1 according to the invention is particularly safe to handle for the therapist; the patient only feels the piercing of the thin and short needle electrodes 6 and 7, which is not particularly painful. The varices 11 with small varicose dilatations of the cutaneous veins are thoroughly and safely obliterated, whereby no permanent, cosmetically unattractive changes appear on the surface of the top skin 13.

I claim:

1. Electrosurgical instrument for the therapy of varices, comprising two fork-shaped protruding needle electrodes (6, 7), which are connectable to different poles of an electrical current source and which each are partly coated by a thin electrical insulation layer, said insulation layer leaving a forward tip zone (6a, 7a) of the needle electrodes (6, 7) free, whereby the transition from the tip zone to an insulated zone is substantially stepless; and the needle electrodes (6, 7) are axially supported at a rearward end in insulating sleeves (4, 5) having a larger cross section than the needle electrodes (6, 7).

2. Instrument according to claim 1, further comprising an electrode head and a grip piece, wherein the insulating sleeves (4, 5) form legs of the approximately trouser-shaped electrode head (2), on which the needle electrodes (6, 7) are mounted;

said electrode head having a leg side and said needle electrodes are mounted on the leg side directed in a forward direction, and said electrode head rearwardly is connected with said grip piece (3) which is pen-shaped.

3. Instrument according to claim 2, wherein the electrode head (2) and the grip piece (3) have corresponding electrical and mechanical connection elements (10, 10a, 10b), the latter being detachably connected with each other.

4. Instrument according to claim 2, further comprising supply lines (8) for the needle electrodes and wherein an electrical manual switch (9) is located in the grip piece (3), said manual switch being integrated in the supply lines (8) of the needle electrodes (6, 7).

5. Instrument according to claim 1, further comprising supply lines (8) of the needle electrodes (6, 7), and a footswitch located in said supply lines (8).

* * * * *